(12) United States Patent
Kim et al.

(10) Patent No.: US 9,371,354 B2
(45) Date of Patent: Jun. 21, 2016

(54) DNA-LINKED NANOPARTICLE BUILDING BLOCKS FOR NANOSTRUCTURE ASSEMBLY AND METHODS OF PRODUCING THE SAME

(71) Applicants: Jin-Woo Kim, Fayetteville, AR (US); Russell Jerry Deaton, Fayetteville, AR (US); Jeong-Hwan Kim, Fayetteville, AR (US)

(72) Inventors: Jin-Woo Kim, Fayetteville, AR (US); Russell Jerry Deaton, Fayetteville, AR (US); Jeong-Hwan Kim, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 13/690,305

(22) Filed: Nov. 30, 2012

(65) Prior Publication Data
US 2013/0136925 A1 May 30, 2013

Related U.S. Application Data

(60) Provisional application No. 61/564,959, filed on Nov. 30, 2011.

(51) Int. Cl.
| | |
|---|---|
| *C07H 21/04* | (2006.01) |
| *B82Y 30/00* | (2011.01) |
| *B82Y 40/00* | (2011.01) |
| *B82B 3/00* | (2006.01) |

(52) U.S. Cl.
CPC .............. *C07H 21/04* (2013.01); *B82B 3/0033* (2013.01); *B82B 3/0057* (2013.01); *B82Y 30/00* (2013.01); *B82Y 40/00* (2013.01); *Y10S 977/774* (2013.01); *Y10T 428/2991* (2015.01)

(58) Field of Classification Search
CPC ..... B82Y 30/00; C07H 21/04; Y10S 977/774
USPC ........... 514/44 R; 977/774; 427/180; 428/403
See application file for complete search history.

(56) References Cited

U.S. PATENT DOCUMENTS

| | | | |
|---|---|---|---|
| 7,485,419 | B2 | 2/2009 | Lu et al. |
| 2003/0207296 | A1 | 11/2003 | Park et al. |
| 2009/0246142 | A1 | 10/2009 | Bhatia et al. |
| 2009/0258355 | A1 | 10/2009 | Maye et al. |
| 2010/0170612 | A1 | 7/2010 | Velegol et al. |
| 2010/0303874 | A1 | 12/2010 | Akcora et al. |

OTHER PUBLICATIONS

Mirkin, et al., "A DNA-based method for rationally assembling nanoparticles into macroscopic materials" Nature 1996, 382, 607-609.*
Kim et al., "Simultaneously Controlled Directionality and Valency on a Water-Soluble Gold Nanoparticle Precursor for Aqueous-Phase Anisotropic Self-Assembly" Langmuir 2010, 26, 18634-18638.*
Taton et al. J. Am. Chem. Soc. 2000, 122, 6305-6306.*
Ackerson, et al., "Defined DNA/nanoparticle conjugates" Proc. Natl. Acad. Sci. 2005, 102, 13383-13385.
Adleman, "Molecular Computation of Solutions to Combinatorial Problems" Science 1994, 266, 1021-1024.
Adleman, et al., "Combinatorial Optimization Problems in Self-Assembly" In Proc. 34th ACM symposium on Theory of Computing (STOC2002), ACM Press, New York, New York, 2002, 23-32.
Aldaye, et al., "Assembling Materials with DNA as the Guide" Science 2008, 321, 1795-1799.
Boyle, "Scientists build with DNA bricks" NBCNews.com, <http://cosmiclog.nbcnews.com/_news/2012/11/29/15544581-scientists-build-with-dna-bricks?lite>, Nov. 30, 2012 (4 pages).
Chen, et al., "Synthesis from DNA of a molecule with the connectivity of a cube" Nature 1991, 350, 631-633.
Deaton et al., "Design and test of noncrosshybridizing oligonucleotide building blocks for DNA computers and nanostructures" J. Chen, Appl. Phys. Lett. 2003, 82, 1305-1307.
Deaton, et al., "Reliability and Efficiency of a DNA-Based Computation" Jr., Phys. Rev. Lett. 1998, 80, 417-420.
Ding, et al., "Gold Nanoparticle Self-Similar Chain Structure Organized by DNA Origami" J. Am. Chem. Soc. 2010, 132, 3248-3249.
Douglas et al., "Self-assembly of DNA into nanoscale three-dimensional shapes" Nature, 2009, 459, 414-418.
Gittins et al., "Spontaneous Phase Transfer of Nanoparticulate Metals from Organic to Aqueous Media" Angew. Chem. Int. Ed. 2001, 40, 3001-3004.
Hung, et al., "Large-area spatially ordered arrays of gold nanoparticles directed by lithographically confined DNA origami" Nat. Nanotechnol. 2010, 5, 121-126.
Jones et al., "DNA-nanoparticle superlattices formed from anisotropic building blocks" Nat. Mater. 2010, 9, 913-917.
Kim et al., "Sequential Solid-Phase Fabrication of Bifunctional Anchors on Gold Nanoparticles for Controllable and Scalable Nanoscale Structure Assembly" Langmuir 2008, 24, 5667-5671.
Kim, et al., "Estimating the sequence complexity of a random oligonucleotide population by using in vitro thermal melting and Cot analyses" Nanomedicine 2005, 1, 220-230.
Macfarlane, et al., "Establishing the Design Rules for DNA-Mediated Programmable Colloidal Crystallization" Angew. Chem. Int. Ed. 2010, 49, 4589-4592.
Maune et al., "Self-assembly of carbon nanotubes into two-dimensional geometries using DNA origami templates" Nat. Nanotechnol. 2010, 5, 61-66.
Nykypanchuk, et al., "DNA-guided crystallization of colloidal nanoparticles" Nature 2008, 451, 549-552.

(Continued)

*Primary Examiner* — Janet Epps-Smith
(74) *Attorney, Agent, or Firm* — Michael Best & Friedrich LLP (57) ABSTRACT

A method of producing a nanoparticle assembly. The method includes attaching a first DNA molecule to a bead to form a first DNA-bead complex; and combining a nanoparticle with the first DNA-bead complex to form a nanoparticle-DNA-bead complex having one DNA molecule attached to the nanoparticle.

20 Claims, 8 Drawing Sheets

(56) References Cited

OTHER PUBLICATIONS

Park, et al., "DNA-programmable nanoparticle crystallization" Nature 2008, 451, 553-556.

Pinto, et al., "Sequence-Encoded Self-Assembly of Multiple-Nanocomponent Arrays by 2D DNA Scaffolding" Nano Lett. 2005, 5, 2399-2402.

Rothemund, et al., "Folding DNA to create nanoscale shapes and patterns" Nature, 2006, 440, 297-302.

Sardar et al., "Asymmetrically Functionalized Gold Nanoparticles Organized in One-Dimensional Chains" Nano Lett. 2008, 8, 731-736.

Schulman, et al., "Programmable Control of Nucleation for Algorithmic Self-Assembly" SIAM J. Comput. 2009, 39, 1581-1616.

Sharma, et al., "Toward Reliable Gold Nanoparticle Patterning on Self-Assembled DNA Nanoscaffold" J. Am. Chem. Soc. 2008, 130, 7820-7821.

Suzuki, et al., "Controlling the No. And Positions of Oligonucleotides on Gold Nanoparticle Surfaces" J. Am. Chem. Soc. 2009, 131, 7518-7519.

Tang, et al., "One-Dimensional Assemblies of Nanoparticles: Preparation, Properties, and Promise" Adv. Mater. 2005, 17, 951-962.

Toffoli, et al., "Programmable Matter: Concepts and Realization" Physica D 1991, 47, 263-272.

Whitesides, et al., "Self-Assembly at All Scales" Science, 2002, 295, 2418-2421.

Winfree, et al., "Design and self-assembly of two-dimensional DNA crystals" Nature, 1998, 394, 539-544.

Winfree, et al., "The Program-Size Complexity of Self-Assembled Squares" In Proc. 32nd ACM symposium on Theory of Computing (STOC2000), ACM Press, New York, New York, 2000, 459-468.

Winfree, et al., "Universal Computation via Self-Asembly of DNA: Some Theory and Experiments" In DNA Based Computers, vol. 44, of DIMACS (Eds: L. F. Landweber E. B. Baum), AMS press, Providence, Rhode Island, 1998, 191-213.

Yu, et al., "Independent Sets of DNA Oligonucleotides for Nanotechnology Applications" IEEE Trans Nanobioscience 2010, 9, 38-43.

Zhao, et al., "Encapsulation of Gold Nanoparticles in a DNA Origami Cage" Angew. Chem. Int. Ed. 2011, 50, 2041-2044.

Kim, J.-W. et al., "Molecular self-assembly of multifunctional nanoparticle composites with arbitrary shapes and functions: challenges and strategies," Part. Part. Syst. Charact. (2013) 30:117-132.

* cited by examiner

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic

```
<400> SEQUENCE: 1
aacgaacctt ctagagtatg                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
catactctag aaggttcgtt                                              20
```

DNA-LINKED NANOPARTICLE BUILDING BLOCKS FOR NANOSTRUCTURE ASSEMBLY AND METHODS OF PRODUCING THE SAME

CROSS-REFERENCE TO RELATED APPLICATIONS

This application claims priority to provisional application no. 61/564,959, filed Nov. 30, 2011, which is incorporated herein by reference in its entirety.

GOVERNMENT SUPPORT

This invention was made with government support under CMMI-0709121 awarded by the National Science Foundation. The Government has certain rights in the invention.

BACKGROUND

The present invention relates to nanoparticle assemblies and methods of making nanoparticle assemblies.

Programmable matter is a distributed system of agents that act cooperatively to configure themselves into arbitrary shapes with arbitrary functions. The molecular self-assembly of structures containing many nanoparticles is a candidate for programmable matter. Programmability implies that system designers are able to control the properties of assembly products. The system should be able to assemble arbitrary, anisotropic shapes, like an electronic circuit, with the capability of incorporating different materials at specific locations within the structure. Defects or errors should be minimized and three-dimensional (3D) assembly should be possible. In self-assembly, component parts, or building blocks, interact locally to produce a coherent and organized whole. At the molecular level, the interactions are determined by "patches" that react between building blocks. Frequently, the assemblies exhibit collective properties that are distinct from those of their constituent components. These properties often depend upon the shape of the structure. Thus, the difficulty of programmability is really the difficulty of controlling the shape of resulting nanostructures. The ability to program the shape of a final assembly is computationally hard and subject to frequent errors. Nevertheless, through careful design and implementation of building blocks, desired shapes and properties might be achieved. To maximize programmability (i.e., control), there should be a large number of types of patches available. Otherwise, there is not the variety of interactions to assemble complicated shapes. The placement and relative orientation of patches on the surface of the building block should be controlled. Different types of patches should be able to be placed on the same building block to diversify the shapes available. Finally, the chemistry for patch conjugation to the building block should be relatively simple and sustainable, and should be able to be used with a variety of materials.

As a result of its unique molecular recognition properties, structural features, and ease of manipulation, DNA has been considered as a promising material to achieve programmable assembly of nanostructures. Nanoparticle (NP) building blocks with different surface functionalities for DNA linkers have been reported. Results with DNA computing verified the programmability of nanotechnology based upon DNA and showed that DNA self-assembly was computationally universal. DNA programmability has demonstrated the ability to assemble a variety of shapes and, when NPs are incorporated, to control the position of NPs in linear, two-dimensional (2D), and 3D assemblies including those based upon origami techniques. Nevertheless, the rational self-assembly of functional structures with arbitrary shapes in all dimensions and at all scales, which can incorporate many different NPs into a variety of final geometries, remains difficult to attain.

SUMMARY

Accordingly, in one embodiment the invention provides a method of producing a nanoparticle assembly. The method includes attaching a first DNA molecule to a bead to form a first DNA-bead complex; and combining a nanoparticle with the first DNA-bead complex to form a nanoparticle-DNA-bead complex having one DNA molecule attached to the nanoparticle.

In another embodiment, the invention provides a nanoparticle assembly. The nanoparticle assembly includes a first nanoparticle having a first and a second DNA molecule attached on opposite sides thereof, the first and second DNA molecules being approximately parallel to one another.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Embodiments of the invention include strategies for controlling geometry of nano-assembly and the functions of nanoparticle assemblies on the basis of an aqueous-phase anisotropic functionalization technique. The technique produces building blocks for assembly of nanostructures which permits greater control over geometry and more complex functionality than existing methods by placing DNA linkers at well-defined and repeatable locations on a nanoparticle (NP). The disclosed techniques can be used to incorporate many different materials into a variety of final geometries and places the linkers on the NP within specific angles of each other, producing building blocks with well-defined arrangements of DNA in all dimensions. This new methodology for anisotropic functionalization of DNA can be used as the basis for fabricating "programmable" and "customized" building blocks of NPs, making the DNA-guided assembly process more reproducible and scalable, and allowing the assembly of complex hybrid nanoscale architectures at all scales, as well as in all dimensions. The DNA-linked building blocks and their self-assembled nano-composites can address the urgent need in the field of nanotechnology for functional, reliable, and scalable techniques for more complicated and controlled multifunctional nanostructures that incorporate other nanocomponents for specific applications. This technology provides an effective and efficient route to a "second-generation" multifunctional nano-architecture with multiplex, multicolor, and multimodal properties that are "programmable/customizable" on the basis of the target biomedical applications. The nanoscale building block based technology can also transform many fields of research including biology, medicine, chemistry, physics, and materials science and engineering.

Figure 1A:
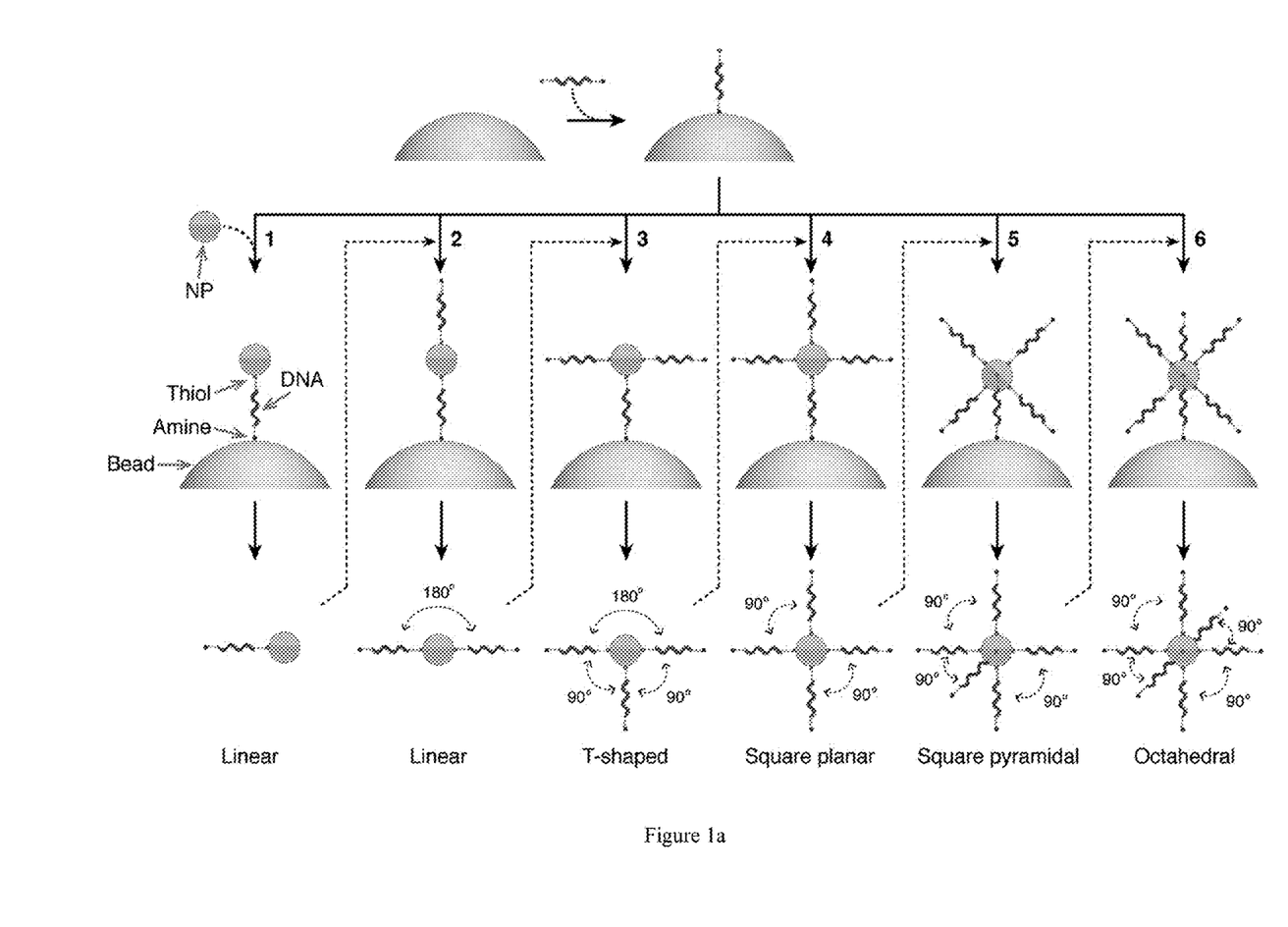
FIG. 1a shows a schematic of an experimental design for the synthesis of DNA-linked gold nanoparticle building blocks (nBLOCKs) with up to 6-fold symmetry, according to embodiments of the invention.

In various embodiments, the invention includes strategies to control the number, placement, and relative orientation of DNA linkers on the surface of a colloidal NP building block to maximize its programmability, and realize enhanced control over the shape and function of final self-assembled structures. FIG. 1a shows a schematic illustration of the assembly sequence to produce the DNA-linked colloidal gold (Au) NP building blocks (termed nBLOCKs) with up to 6-fold symmetry according to embodiments of the invention. Numbers represent the sequences of the aqueous-phase anisotropic sequential ligand replacement strategy. In one embodiment, the DNA oligonucleotide linker (curved line) has chemically modified amine (dot labeled 'amine') and thiol (dot labeled 'thiol') ends. The smaller circle (labeled 'NP') is a gold NP co-modified with DMAP and MESA capping ligands, and the larger circle (labeled 'bead') represents 4-carboxylbutyl-functionalized silica gel. In various embodiments, other materials can be used in place of silica gel, including, without limitation, similarly-functionalized magnetic particles, membranes, polymer resins, polystyrene microarrays, glasses, micas, or porous beads. DNA was attached to the NP one by one. Thus, a NP with one DNA was the starting material for the second DNA attachment. The incoming DNA maximally segregated from the existing DNA, producing an angle of approximately 180° between them, i.e. the two DNA molecules are approximately parallel to one another. According to embodiments of the invention, two DNA molecules are approximately parallel or approximately 180° apart if the angle between the DNA molecules is within no more than 1°, no more than 2°, no more than 3°, no more than 4°, no more than 5°, or no more than 10° from 180°. This complex was then used as the starting material for the third DNA attachment. To maximally segregate from the two existing DNA molecules, the third DNA molecule attaches at an angle of approximately 90° from the first two, i.e. the third DNA molecule is approximately perpendicular to the other two DNA molecules, producing T-shaped structures as shown. According to embodiments of the invention, two DNA molecules are approximately perpendicular or approximately 90° apart if the angle between the DNA molecules is within no more than 1°, no more than 2°, no more than 3°, no more than 4°, no more than 5°, or no more than 10° from 90°. Likewise, attachment of a fourth DNA produces a NP with DNA molecules at approximately 90° from each other, i.e., a square planar arrangement. Subsequent attachments proceed in this fashion, producing the identified geometries, as described further below.

A measure of control was achieved based upon the sequential ligand replacement approach and the use of relatively stiff DNA linkers, which were shorter than the persistence length of double-stranded DNA, which in various embodiments is approximately 50 nm. In some embodiments, the DNA linkers ranged from about 15 to about 25 nucleotides in length. In other embodiments, the DNA linkers ranged from about 5, about 10, about 20, about 30, about 40, about 50, about 60, about, 70, about 80, about 90, about 100, about 110, about 120, about 130, about 140, or about 150 nucleotides in length, although other lengths are also possible. Each DNA linker may have a different length in order to increase the complexity of the assemblies that are generated.

Figure 1B:
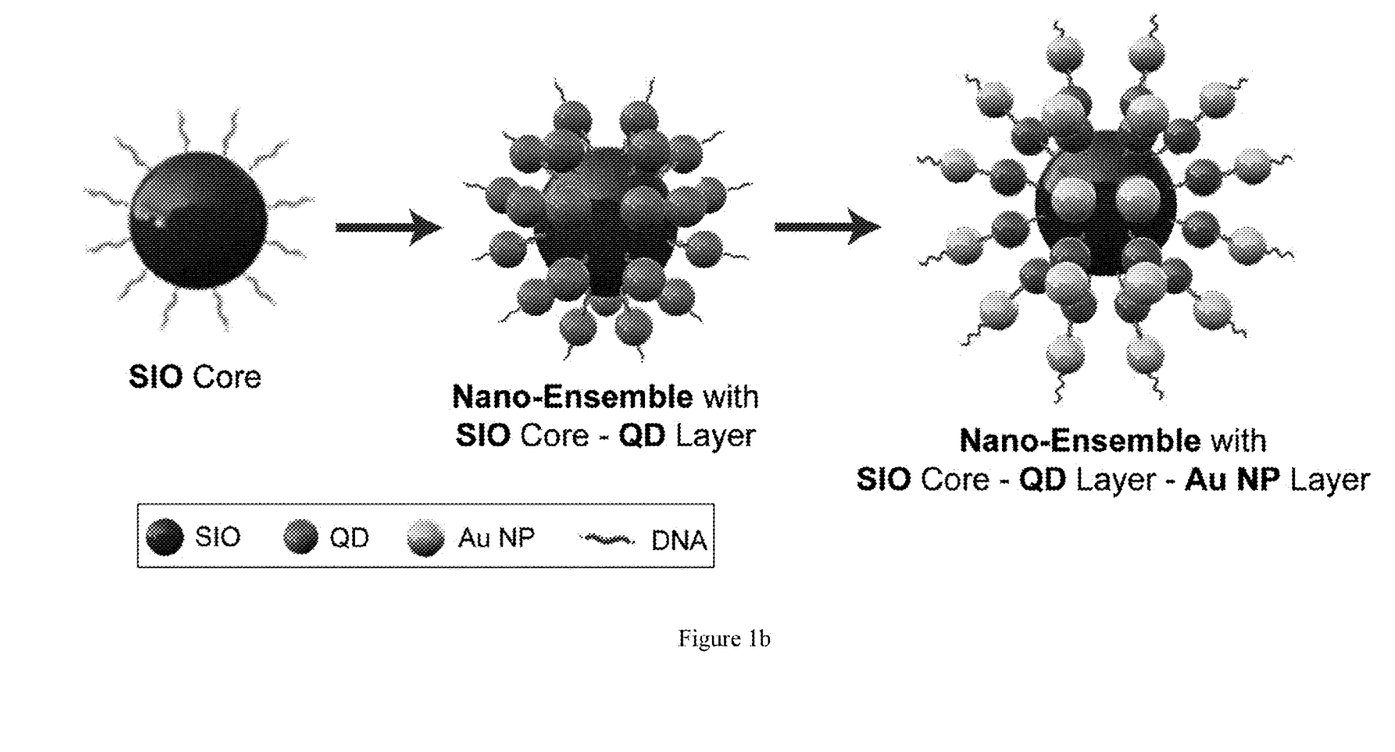
FIG. 1b shows schematic representations of DNA-directed self-assembly of nBLOCKs to produce a possible 3D spherical multifunctional hybrid nanocomposite which incorporates superparamagnetic iron oxide (SIO), quantum dot (QD), and gold (Au) NP layers.

In the assembly reaction, the electrostatic repulsions as well as steric hindrances of DNA molecules influence the layout of DNA on a NP. The net charge of DNA at pH above its isoelectric point (i.e., ~5) is negative, so DNA molecules under these conditions tend to position on a NP to minimize the mutual electrostatic repulsions (e.g. analogous to the Valence Shell Electron Pair Repulsion model), contributing to the molecular geometry. In addition, steric hindrance effects between the DNA molecules further constrains the overall geometry, particularly using small NPs. In various embodiments of the present invention, NP diameter ranged from about 1 nanometer to about 30 nanometers, and in one particular embodiment the average NP diameter was approximately 3 nanometers. Thus, in various embodiments, the NP diameter is about 1 nm, about 2 nm, about 3 nm, about 4 nm, about 5 nm, about 10 nm, about 15 nm, about 20 nm, about 25 nm, or about 30 nm, although other diameters are also possible. Although the examples herein use gold-based nanoparticles, other materials can also be used including, without limitation, iron oxide magnetic nanoparticles, superparamagnetic iron oxide (SIO) nanoparticles, quantum dots, C60 (Buckminsterfullerene), or other metallic nanoparticles, such as silver, platinum, ruthenium, or palladium. In various embodiments, the nanoparticles may have various shapes such as a sphere, square, rod, or prism, which can influence the properties and morphology of the final nanoparticle assembly. Final nanoparticle assemblies may be cube-shaped or spherical and may incorporate combinations of different types of particles including a SIO core, a first layer of quantum dots (QD), and a second layer of NPs (see, e.g., FIG. 1b). In some embodiments the NPs may be coupled to one another via DNA linkages.

Figure 5A:
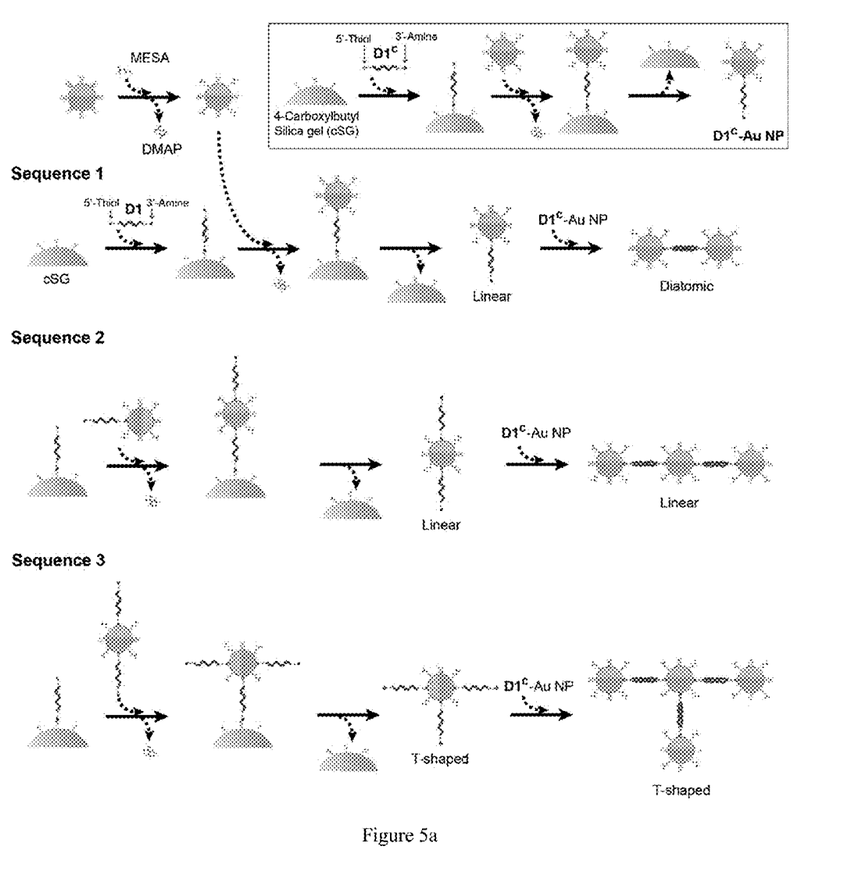
FIGS. 5a and 5b show a schematic of the steps of the anisotropic aqueous-phase ligand replacement method according to embodiments of the invention.
Figure 5B:
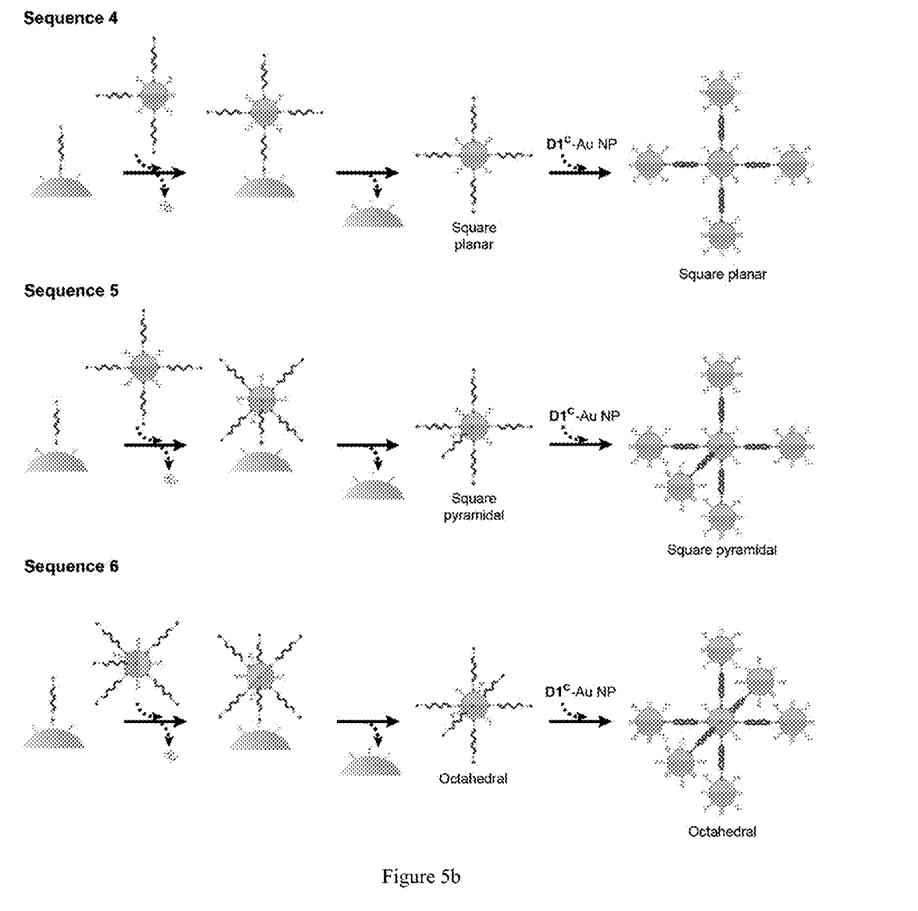

In various embodiments, DNA is functionalized to a gold NP in a stepwise manner: for example, a NP with one DNA is the starting material for the second DNA attachment, a NP with two DNA is the starting material for the third DNA attachment, and so on (see FIGS. 1, 5a, and 5b). With this constraint, the position of DNA attachment occurs in a manner that minimizes electrostatic and steric interactions of the newly-added DNA molecule with the existing DNA molecules on the NP, yielding the optimal arrangement of DNA on an NP with up to six-fold symmetry, that is, linear (1 and 2 DNA), T-shaped (3 DNA), square planar (4 DNA), square pyramidal (5 DNA), and octahedral (6 DNA) (FIG. 1a; see FIGS. 5a and 5b). In the absence of such a constraint (i.e., simultaneous DNA attachment), the arrangement of 3, 4, and 5 DNA would tend to be trigonal planar, tetrahedral, and trigonal bipyramidal, respectively. Instead, the sequential, one-by-one attachment strategy produces different geometries as opposed to the simultaneous attachment, yielding the configurations shown in FIG. 1a.

Figure 2:
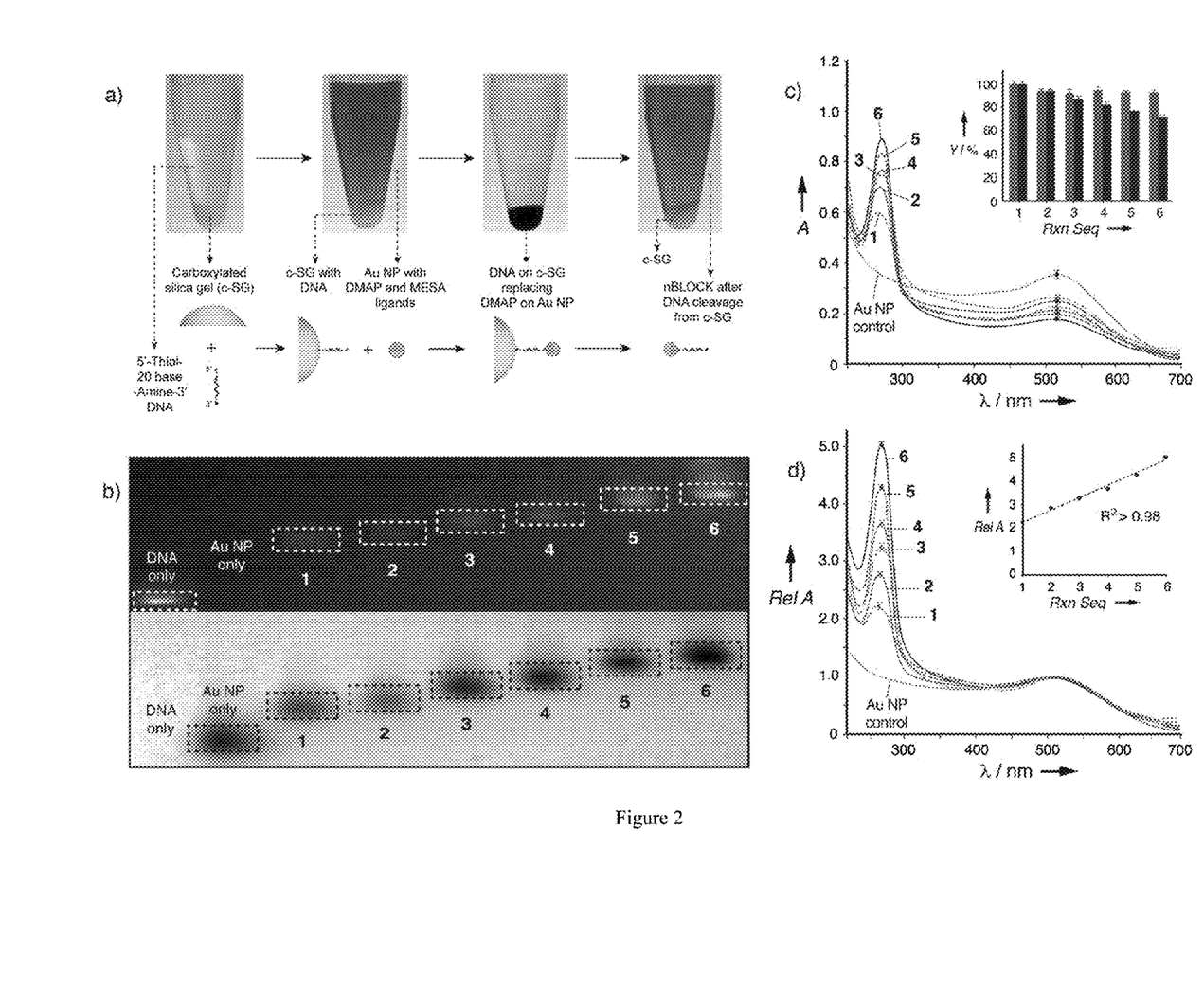
FIGS. 2a through 2d show analyses of an nBLOCK assembly process according to embodiments of the invention.

FIGS. 2a through 2d show analyses of an nBLOCK assembly process according to embodiments of the invention. FIG. 2a shows the reaction solutions with schematics during the first sequence of the DNA functionalization process (see FIGS. 1, 5a, and 5b), which was designed based upon the silica-gel based aqueous-phase anisotropic ligand replacement strategy. By repeating the process, control over the DNA linker's number, location, and orientation on the NP could be achieved. The functionalization reaction occurred in a mild aqueous condition and at ambient temperature, and one reaction sequence could be completed in an hour. Also non-specific adsorptions and/or interactions between DNA, Au NP, and silica gel were very minimal. Such a rapid, efficient, and mild reaction in an aqueous solution contributes to a sustainable chemistry of reagents in the reaction, including Au NP capping ligands, silica gels, and chemically modified DNA linkers (see Example 1 below). Also of note is the excellent aqueous solubility and chemical stability of Au NPs and nBLOCKs during the ligand replacement reactions (FIG. 2a). Moreover, no apparent changes in the physical and chemical properties of the nBLOCKs were observed at least for a month when stored at 4° C. In various embodiments, alternative capping ligands, such as deoxynucleotide triphosphate (dNTP), can be employed to increase Au NP stability. For example, the dATP-capped Au NPs were stable up to 10 days at temperatures of 25-90° C. in biologically-relevant phosphate-buffered saline with between 0.1-3 mM NaCl.

It is expected that the aqueous-phase anisotropic functionalization strategy will be applicable to other NPs, particularly when the other NPs have their surface capped with a self-assembled monolayer of polymeric ligands with chemical head groups (i.e., thiol, amine, or phosphine), demonstrating the versatility of the disclosed techniques. In various embodiments, other groups can be used to cap the surface of the NPs, including other short ligand groups that have relatively weak affinity to enable the ligand replacement, and other groups generated from catalytic ion interactions, e.g., from a reaction in which one ligand (i.e., a coating ion, $-SO_4^-$, $SCN^-$, $Cl^-$, $OH^-$, $NH_3^+$) in a complex ion (e.g., metal cation) is replaced by a simple ion.

FIG. 2b shows agarose gel images of nBLOCKs under UV (top) and visible (bottom) light. The numbers 1-6 represent bands containing nBLOCKs with one to six DNA molecules attached thereto (D1; see Table 1). UV light imaging of the ethidium bromide staining (to reveal DNA) of the agarose gel containing nBLOCKs revealed not only the association of DNA with nBLOCKs but also the increases of their molecular weights as the amount of functionalization increased, confirming that the disclosed methods control the number of DNA molecules per gold NP. Also, as the geometric dimension of nBLOCK increased, their mobility decreased exponentially (i.e., the amount of separation of lanes 1 [1D] and 2 [1D] vs. that of lanes 2 [1D] and 3 [2D] vs. that of lanes 4 [2D] and 5 [3D]), indicating successful assembly of the geometric configurations. In addition, the relatively well-defined bands with minimal backgrounds demonstrate the high level of purity of the synthesized nBLOCKs as well as their outstanding solubility and monodispersity in water. Some smearing of bands was visible for the more complex and bulkier 3D nBLOCKs (particularly lane 6, with 6 DNA). The results of optical spectral analyses (FIGS. 2c and 2d) were in good agreement with those of the gel electrophoresis.

FIG. 2c shows optical spectra of nBLOCKs at different laser wavelengths. The inset of FIG. 2c shows the estimated yield at each sequence (left hand bar of each pair) and overall yield after the sequence (right hand bar of each pair). FIG. 2d shows the normalized optical spectra of nBLOCKs at different laser wavelengths. The inset of FIG. 2d shows the DNA concentration profile during the ligand replacement reaction sequences. The numbers in FIGS. 2c and 2d represent the sequences of the ligand replacement method, as in FIG. 1a. Error bars represent the standard deviation based on five measurements.

All nBLOCKs exhibit peaks both at ~260 nm for DNA and at ~530 nm for Au NPs, indicating successful functionalization of DNA to Au NP surface. According to the optical spectra of Au NP at ~530 nm, the yield of nBLOCKs at each sequence was in the range of 92-95% (FIG. 2c, inset; see Example 2), verifying the high efficiency of the disclosed aqueous-phase ligand replacement method. Incorporation of a separation process, such as gel extraction, size-exclusion chromatography, etc., would even further improve the product purity and yield. Also the relative optical spectra at a fixed concentration of Au NP (FIG. 2d) showed almost linear increase of DNA peaks after each functionalization sequence, clearly confirming the capability of the disclosed methods to control the numbers of DNA on a gold NP.

Figure 3:
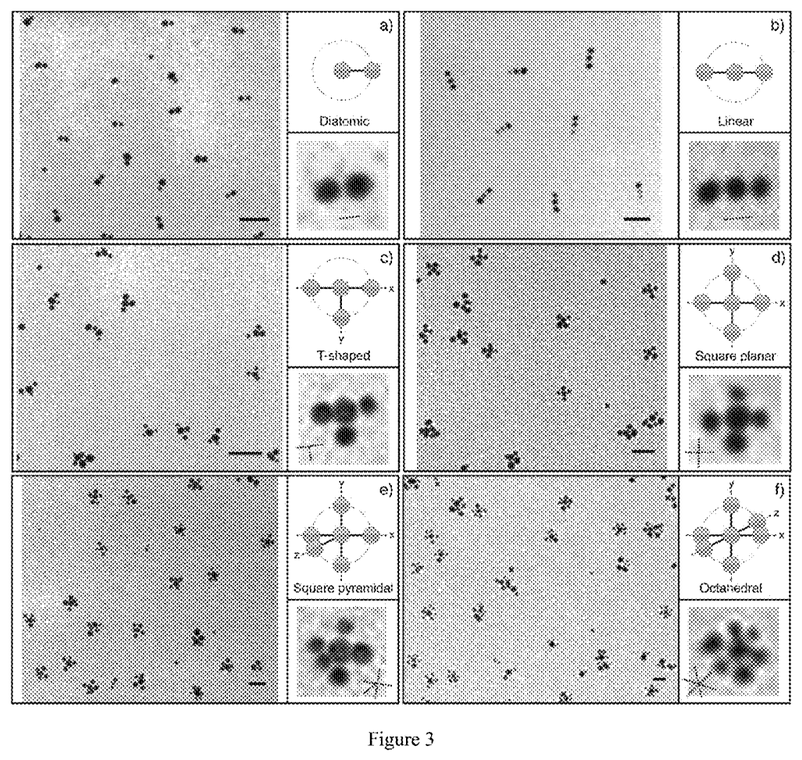
FIGS. 3a through 3f show the molecular geometry of nBLOCKs visualized by transmission electron micrograph (TEM) along with a corresponding schematic representation.

To assess the molecular geometry of the functionalized DNA in nBLOCKs, an Au NP with one complementary DNA sequence was hybridized with each nBLOCK. Transmission electron microscopy (TEM) image analyses revealed that the molecular geometry of NPs in the self-assembled structures was diatomic for nBLOCK with 1 DNA, linear for 2 DNA, T-shaped for 3 DNA, square planar for 4 DNA, square pyramidal for 5 DNA, and octahedral for 6 DNA (FIG. 3).

FIGS. 3a through 3f show the molecular geometry of DNA-linked colloidal gold nanoparticle building blocks (nBLOCKs) visualized by transmission electron micrograph (TEM) along with a corresponding schematic representation of the structure. Each nBLOCK was hybridized with a mono-functionalized nBLOCK with a single complementary DNA oligonucleotide (D1$^c$; see Table 1) to help visualize the structure. The left panels of FIGS. 3a through 3f show TEM images of the self-assembled structures (scale bars represent 20 nm). The bottom right panels of FIGS. 3a through 3f show magnified TEM images of a representative structure. The top right panels of FIGS. 3a through 3f show a schematic illustration of the respective assembled structure, showing nBLOCKs with up to 6-fold symmetry (all x-, y-, and z-directions). In each schematic diagram, the solid line represents double stranded DNA and the dotted circle represents the 2D plane.

The average interparticle lengths (9.7 nm±3.94 nm) of one-dimensional (1D) and 2D structures were in agreement with the calculated interparticle length (ca. ~11 nm). The angles between three particles across two DNA linkages were, on average, 173.9° (±9.88°) for the linear configurations (FIG. 3b) and 84.9° (±8.68°) and 173.2 (±10.01°) for T-shaped and square planar configurations (FIG. 3c-3d; see Example 3), demonstrating the high degree of control of the disclosed methods over the orientation and spatial arrangement of DNA linkers in assembled nBLOCKs. Interparticle lengths and angles for 3D structures were not assessed due to technical limitations in evaluating TEM images with 3D structures. However, TEM images with accompanying schematic illustrations (FIG. 3e-3f and FIG. 4) provide evidence for the formation of 3D square pyramidal and octahedral geometries. While other geometries are visible in the TEM images, this may have been caused by flexibility in the DNA linking NPs or depth effects producing foreshortening of the structure's geometry. Nevertheless, given the one-by-one functionalization method for DNA, the anchor point of DNA on an NP in each step is expected to be approximately 90° or approximately 180° to that of the adjacent DNA existing on the NP in order to achieve their maximal segregations for minimal electrostatic and steric interactions.

In summary, various embodiments of the invention include methods for assembling DNA linkers on an NP within specific angles of each other and producing NP building blocks with well-defined arrangements of DNA in all dimensions. The specific numbers and orientations of DNA on NPs allow greater control over the ultimate shape of nanostructures, making DNA-guided self-assembly process more reproducible and scalable and allowing the assembly of complex hybrid nanoscale architectures at all scales, as well as in all dimensions. The reaction was not only highly sustainable by being aqueous phase, but also highly efficient in its implementation.

In various alternative embodiments, the spacing between particles could be tuned by controlling the lengths of DNA and the overall geometry of DNA on an NP by controlling the extent of electrostatic repulsion and steric hindrance between DNA. Different DNA linkers could be placed at different locations on NPs, increasing the size and complexity of the nanostructure to be assembled. For example, each of the six DNA molecules that is conjugated to a NP may be different from the others so that different NPs or other groups may be added to each of the DNA molecules, through hybridization or other mechanisms of attachment to the DNA molecules. The potential errors could be minimized through appropriate DNA sequence design, for example to prevent or minimize cross-hybridization between different functionalized DNAs. Finally, the disclosed methods have promise to generalize to other types of NPs. Therefore, it has the potential to produce NP building blocks with the properties desired in programmable matter, i.e., arbitrary, anisotropic shapes, including 3D, of structures with specific, desired functions, and precision difficult to achieve with existing methods.

It is expected that the manipulation of matter in such a controlled way at the molecular scale will be applicable to other fields, from tissue engineering to new types of electronics, and will be useful for developing a variety of new materials with novel optical, electrical, and structural properties. For example, this technology facilitates the "programmable" self-assembly of multifunctional composites of nanoparticles (NPs) that conform to a specific design for multiplex and multimodal diagnostics and therapeutics. The versatile means to functionalize DNA to various NPs with precise control over the locations and angles of the DNA molecules will lead to the accurate, scalable and high-rate self-assembly of complex hybrid NP composites with desirable multifunctionalities. Although the examples disclosed herein focus on the use of DNA as a linker, in various embodiments other materials can be used as linkers including other nucleotides, e.g., RNA, synthetic polymers, peptide chains, and proteins. Further, in embodiments of the invention any number of groups can be attached at the end of DNA linker including amine, thiol, or biotin groups, including a number of commercially-available and/or proprietary technologies (e.g. such as those available from companies such as Integrated DNA Technologies).

Experimental

Figure 6:
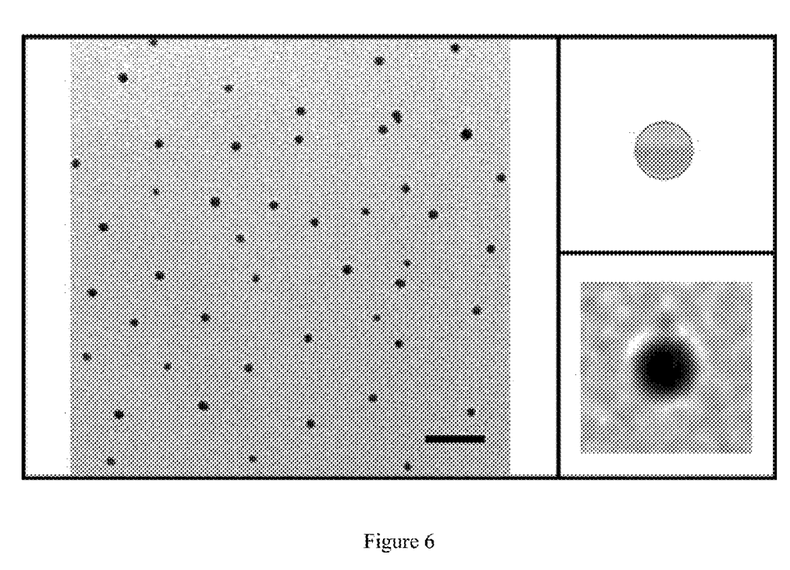
FIG. 6 shows a Au NP co-modified with dimethyl aminopyridine (DMAP) and mercaptoethane sulfonic acid (MESA) capping ligands (scale bar represents 20 nm), where the average diameter was estimated to be 2.83 nm (±0.47 nm).

Water-soluble Au NP synthesis: Water-soluble dimethyl aminopyridine (DMAP) monolayer-protected Au NPs synthesized according to the previously described method (D. I. Gittins, F. Caruso, Angew. Chem. Int. Ed. 2001, 40, 3001-3004, incorporated herein by reference). They were further modified to synthesize a robust and stable mixed monolayer with mercaptoethane sulfonic acid (MESA) ligands according to the previously described ligand exchange method (J.-H. Kim, J.-W. Kim, Langmuir 2010, 26, 18634-18638, incorporated herein by reference) to enhance their chemical stability during DNA functionalization process. The final concentration of the resultant Au NPs co-modified with DMAP and MESA ligands was estimated to be 6 µM in water according to ultraviolet/visible/near-infrared (UV/vis/NIR) spectral analysis ($\epsilon$=~1×106 M-1 cm-1). The Au NPs showed excellent solubility in biological buffer solutions (FIG. 2a) and a net negative charge according to the gel electrophoresis (FIG. 2b). Estimated with TEM, the ligand capped Au NP was well dispersed with average diameter of 2.83 nm (±0.47 nm) (FIG. 6).

Synthesis of DNA-linked nBLOCKs: A DNA oligonucleotide and its complementary sequence with chemically modified 3' and 5' ends were designed and purchased from Integrated DNA Technologies. The oligonucleotide sequences are summarized in Table 1 in the Supporting Information. The 4-carboxylbutyl-functionalized silica gels (cSGs) were purchased from Silicycle. The disclosed DNA functionalization technique (FIGS. 1, 2a, 5a, and 5b) starts with electrostatically binding the positively charged amine end of DNA to the negatively charged surfaces of cSGs. Briefly, the reaction mixture consisted of 3.97 mM DNA and 50 mg cSGs in 1 mL 10 mM boric acid buffer (pH 7.4), and was incubated overnight with gentle mixing. The DNA bound cSGs (DNA-cSGs) were then washed by centrifugation/resuspension 3× with 10 mM phosphate buffer with 10 mM NaCl (pH 7.4). Estimated with UV/vis/NIR spectrophotometry, the loading yield of DNA linkers on cSG beads was ~90%. For the ligand replacement reaction, the thiol group at 5'-end of DNA bound to cSGs was activated by adding 400 µL 50 mM dithiothreitol with 2 vol % triethylamine to 1 mL DNA-cSG solution and incubating for 10 min with vigorous agitation. The activated DNA-cSGs were rinsed by centrifugation/resuspension 3× with the phosphate buffer, resuspending to 1 mL phosphate buffer. The ligand replacement reaction was continued by adding 1.2 µM Au NP solution to 1 mL of the activated DNA-cSG solution and incubating for 1 h with gentle shaking. This allowed DNA on silica gels to replace a short DMAP ligand on the Au NP, making the color of cSGs change from white to dark red (FIG. 2a). The Au NPDNA-cSGs were rinsed by centrifugation/resuspension 3× with the boric acid buffer, resuspending to 1 mL ethanol. Finally, the electrostatically bound DNA was released from cSGs by adding 0.5 vol % trifluoroacetic acid with gentle mixing for ~30 s. This effectively cleaved DNA from cSGs, making the color of solution red (FIG. 2a). The resultant mono-functionalized Au NP nBLOCKs with one DNA were rinsed by centrifugation/resuspension 3× with 1 mL water and resuspended in 1 mL 10 mM Tris buffer (pH 7) for the next sequence of functionalization. For the second functionalization sequence, the above steps were repeated with a modification. The DNA-cSGs were suspended in the Tris buffer instead of the phosphate buffer to block free (i.e., unoccupied) carboxyl groups on cSGs, alleviating the undesirable nonspecific interactions between carboxyl groups on cSGs and amine groups of DNA in nBLOCKs. By repeating the process with this change, the DNA linker's number, location, and orientation on the NP could be controlled up to a 6-fold symmetry. The DNA-linked nBLOCKs synthesized in this study include Au NPs with one to six D1 and those with one $D1^c$ (see Table 1).

Assessment of nBLOCKs: The DNA-linked nBLOCKs were concentrated 10× by centrifugation and resuspension with the Tris buffer, and analyzed using 2% agarose gel electrophoresis. The gel was examined under white light as well as UV light after staining with ethidium bromide (FIG. 2b). The optical absorption spectra of nBLOCKs were examined using a DU-800 UV/vis/NIR spectrophotometer (Beckman Coulter) (FIG. 2c). The UV/vis/NIR optical spectra were normalized on the absorption of Au NPs at ~530 nm in the wavelength range of 230 and 700 nm (FIG. 2d). Additionally, each of the six D1-linked nBLOCKs was hybridized with Au NPs with one $D1^c$ to assess its molecular geometry. For the hybridization reactions, equi-volumes of D1-linked nBLOCKs and Au NPs with $D1^c$ in the Tris buffer were mixed and incubated for 1 h at 25° C. The physical characteristics of the self-assembled structures were assessed with TEM (see Methods below).

EXAMPLES

Example 1

FIGS. 5a and 5b show a schematic of the steps of the anisotropic aqueous-phase ligand replacement method according to embodiments of the invention. D1 and $D1^c$ represent complementary 20-base DNA molecules with chemically modified 3'-amine and 5'-thiol ends (see Table 1), DMAP=dimethyl aminopyridine, and MESA=mercaptoethane sulfonic acid. The DNA molecules were attached to the NP on a stepwise basis, as disclosed above. As shown in FIGS. 5a and 5b, NPs coupled to DNA molecules and their respective complements can be combined to produce increasingly complex assemblies. Although the diagrams of FIGS. 5a and 5b only depict two types of DNA molecules, labeled as D1 and its complement $D1^c$, in fact each DNA molecule D1 may be distinct from the other DNA molecules in its length as well as sequence, where each DNA molecule has a unique complement $D1^c$, to permit an even higher level of complexity in the formation of NP assemblies. The various DNA molecules D1 and complements thereof $D1^c$ should be selected to reduce or eliminate cross-hybridization in order to obtain the correct assembly with a high degree of accuracy and reproducibility.

The maximal efficiency and specificity of the DNA functionalization process based upon the aqueous-phase anisotropic ligand replacement approach could be achieved through the careful design and/or selection of the chemistry of reagents (FIGS. 1, 2a, 5a, and 5b): (1) negatively charged solid supports (that is, carboxylated silica gels), (2) water-soluble and net negatively charged Au NPs by assembling a mixed layer of weak DMAP (neutrally charged) and strong MESA (negatively charged due to the major influence of the sulfonic acid groups, see R. Sardar, J. S. Shumaker-Parry. Nano Lett. 2008, 8, S1-S4, incorporated herein by reference) capping ligands, and (3) DNA with chemically modified 3'-amine and 5'-thiol ends (Table 1). Relatively weak adsorption affinity of amino head groups of DMAP on Au NP enabled a rapid and efficient ligand exchange with the free thiol end of chemically modified DNA on the silica gel. Weak electrostatic adsorption of the amine end of DNA to carboxylated silica gels allowed releasing DNA within 30 s only using 0.5% TFA with no effect on DNA and its bonding on Au NP. The charge characteristics of the reagents during the functionalization process (i.e., negatively charged silica gels, net negatively charged Au NP, and free —SH groups of net negatively charged DNA bound to the silica gels) alleviated nonspecific interactions between each other. These highly efficient and mild exchange and cleavage reactions with minimal nonspecific interactions contribute to the high production yields of nBLOCKs (FIG. 2c; Example 2).

TABLE 1

DNA sequences

| Name | Sequence |
|---|---|
| D1 | 5'-Thiol-AACGAACCTTCTAGAGTATG-Amine-3' (SEQ ID NO: 1) |
| D1° | 5'-Thiol-CATACTCTAGAA GGTTCGTT-Amine-3' (SEQ ID NO: 2) |

DNA sequences were designed according to established methods (W. Yu, J. S. Lee, C. Johnson, J.-W. Kim, R. Deaton, IEEE Trans. Nanobioscience 2010, 9, 38-43; J.-W. Kim, D. P. Carpenter, R. Deaton, Nanomedicine 2005, 1, 220-230; R. Deaton, J.-W. Kim, J. Chen, Appl. Phys. Lett. 2003, 82, 1305-1307, each of which is incorporated herein by reference). In general, DNA sequences are selected which bind only to their Watson-Crick complement to eliminate binding errors in the structure. The nearest-neighbor model for DNA thermal stability was used in the selection process.

Example 2

The yield of nBLOCK synthesis was assessed on the basis of the optical spectra of Au NPs at ~530 nm after each sequence of the DNA functionalization process (FIG. 2c). The yield of the first sequence to produce mono-functionalized nBLOCKs was ~73% compared to the initial concentration of Au NPs. However, Au NPs were used in excess to maximize the ligand replacements and the residual Au NPs after the functionalization reaction (that is, the remaining Au NPs in solution after its ligand exchange with DNA bound to silica gels) were recycled. Thus, the initial Au NP concentration was not considered for the yield estimation; instead, the overall yields were estimated compared to the concentration of the mono-functionalized nBLOCKs (that is, assuming the yield of the first sequence to synthesize mono-functionalized nBLOCKs as 100%). Table 2 summarizes the yield at each sequence as well as the overall yield after each sequence.

TABLE 2

Yields of nBLOCK synthesis

| Sequence | Yield (%) | | | | | |
|---|---|---|---|---|---|---|
| | 1 | 2 | 3 | 4 | 5 | 6 |
| Yield at each sequence | 100 (±2.80) | 94.3 (±1.61) | 92.2 (±3.58) | 94.9 (±2.89) | 93.3 (±1.17) | 92.9 (±2.21) |
| Overall yield | 100 (±2.80) | 94.3 (±1.61) | 87.0 (±3.38) | 82.5 (±2.51) | 77.0 (±0.96) | 71.5 (±1.70) |

Example 3

The physical characterization of 1D and 2D nBLOCKs in their TEM images (as exemplified in FIGS. 3a-3d), including particle size and interparticle spacing and angle, was performed using Scion Image Software (see Methods below). The interparticle length was defined as the distance between the centers of two adjacent Au NPs. The angles are those between three particles across two DNA bonds. The expected angle of 1D structures (linear) is approximately 180° and that of 2D structures (T-shaped and square planar) is approximately 90° and approximately 180°. The analyzed data are summarized in Table 3.

The interparticle length could be calculated using the length of DNA (that is, 0.33 nm per base pair), the length of C6 linker in the modified DNA (that is, ~0.88 nm) and the average diameter of Au NP (that is, 2.83 nm). The calculated length is ca. ~11 nm.

TABLE 3

Physical characteristics of 1D and 2D nBLOCKs

| nBLOCK | Au NP only | 1 DNA: diatomic | 2 DNA: linear | 3 DNA: T-shaped | 4 DNA: square planar |
|---|---|---|---|---|---|
| Particle size (nm) | 2.83 (±0.47) | — | — | — | — |
| Interparticle spacing (nm) | — | 9.3 (±4.12) | 9.7 (±3.83) | 9.5 (±3.44) | 10.1 (±4.39) |
| Angles (°) | — | — | 173.9 (±9.88) | 174.6 (±8.76) or 85.9 (±9.12) | 171.8 (±11.24) or 83.8 (±8.24) |

The numbers of particles used for analyses were about 100 particles for the size estimation of Au NPs and about 50 interparticle distances and angles of 1D and 2D self-assembled structures. The interparticle spacing is the distance between the centers of two adjacent Au NPs and the angle is that between 3 NPs across 2 DNA bonds in TEM images.

Methods

TEM Imaging and its Characterization

Figure 4:
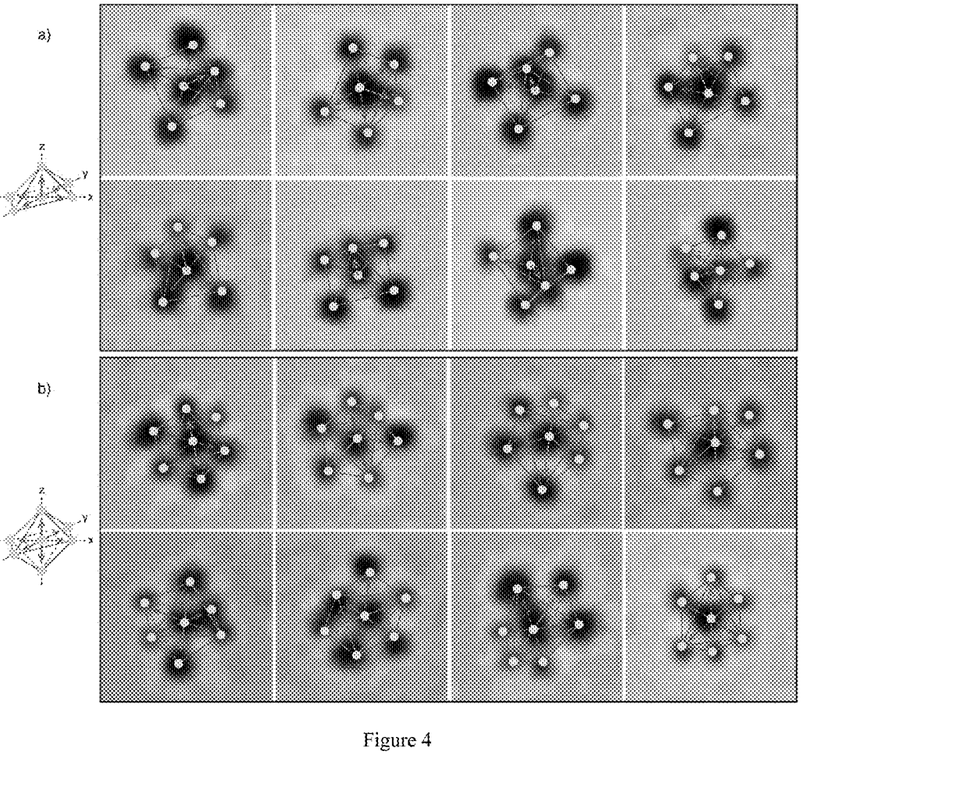
FIG. 4 shows TEM images along with a geometric interpretation of three-dimensional (3D) nBLOCKs, where panel a) shows 3D square pyramidal and panel b) shows a 3D octahedral nBLOCKs after hybridization with a mono-functionalized nBLOCK with a single complementary DNA oligonucleotide and where lines represent geometric trends of the self-assembled structures, providing evidence for the formation of the corresponding 3D geometries.

The TEM analyses were conducted with a JEOL 100CX Electron Microscope (JEOL-USA, Peabody, Mass.). 1.5 µL of each sample solution was deposited onto a 300 mesh Formvar-coated copper grid. No staining was used, to alleviate any possibility of artifacts. After dehydration, the samples were examined using the TEM at 100 keV. Particle size analyses as well as interparticle spacing and angle analyses with the TEM images were performed using Scion Image Software (Alpha 4.0.3.2 version, Scion Corporation, Frederic, Md.). The numbers of particles used for analyses were 100 particles for the size estimation of Au NPs co-modified with DMAP and MESA (as exemplified in FIG. 6) and about 50 interparticle distances and angles of 1D and 2D self-assembled structures (as exemplified in FIGS. 3a-3d). The interparticle lengths and angles for 3D structures could not be assessed due to the technical limitations in evaluating TEM images with 3D structures. However, geometric trends were drawn on the basis of the TEM images to confirm the self assembly of 3D structures and their geometries (FIGS. 3e, 3f, and 4).

Each of the following is incorporated herein by reference:

[1] a) T. Toffoli, N. Margolus, Physica D 1991, 47, 263-272; b) C. Mirkin, R. L. Letsinger, R. C. Mucic, J. J. Storho, Nature 1996, 382, 607-609; c) E. Winfree, F. Liu, L. A. Wenzler, N. C. Seeman, Nature, 1998, 394, 539-544.

[2] G. M. Whitesides, B. Grzybowski, Science, 2002, 295, 2418-2421.

[3] M. R. Jones, R. J. Macfarlane, B. Lee, J. Zhang, K. L. Young, A. J. Senesi, C. Mirkin, Nat. Mater. 2010, 9, 913-917.

[4] Y. Y. Pinto, J. D. Le, N. C. Seeman, K. Musier-Forsyth, T. A. Taton, R. A. Kiehl, Nano Lett. 2005, 5, 2399-2402; Z. Y. Tang, N. A. Kotov, Adv. Mater. 2005, 17, 951-962; H. T. Maune, S. Han, R. D. Barish, M. Bockrath, W. A. Goddard III, P. W. K. Rothemund, E. Winfree, Nat. Nanotechnol. 2010, 5, 61-66; L. Adleman, Q. Cheng, A. Goel, M.-D. Huang, D. Kempe, P. M. de Espanes, P. W. K. Rothemund, In Proc. 34th ACM symposium on Theory of Computing (STOC2002), ACM Press, New York, N.Y., 2002, 23-32; E. Winfree, P. W. K. Rothemund, In Proc. 32nd ACM symposium on Theory of Computing (STOC2000), ACM Press, New York, N.Y., 2000, 459-468.

[5] R. Schulman, E. Winfree, SIAM J. Comput. 2009, 39, 1581-1616; R. Deaton, M. Garzon, R. C. Murphy, J. A. Rose, D. R. Franceschetti, S. E. Stevens, Jr., Phys. Rev. Lett. 1998, 80, 417-420.

[6] J. Chen, N. C. Seeman, Nature 1991, 350, 631-633.

[7] a) C. J. Ackerson, M. T. Sykes, R. D. Kornberg, Proc. Natl. Acad. Sci. 2005, 102, 13383-13385; b) K. Suzuki, K. Hosokawa, M. Maeda, J. Am. Chem. Soc. 2009, 131, 7518-7519; c) S. Y. Park, A. K. R. Lytton-Jean, B. Lee, S. Weigand, G. C. Schatz, C. A. Mirkin, Nature 2008, 451, 553-556; d) D. N. Nykypanchuk, M. M. Maye, D. van der Lelie, O. Gang, Nature 2008, 451, 549-552.

[8] a) L. M. Adleman, Science 1994, 266, 1021-1024; b) E. Winfree, X. Yang, N. C. Seeman, In DNA Based Computers, Vol. 44 of DIMACS (Eds: L. F. Landweber E. B. Baum), AMS press, Providence, R.I., 1998, 191-213.

[9] P. W. K. Rothemund, Nature, 2006, 440, 297-302; S. M. Douglas, H. Dietz, T. Liedl, B. Hogberg, F. Graf, W. M. Shih, Nature, 2009, 459, 414-418.

[10] F. A. Aldaye, A. L. Palmer, H. F. Sleiman, Science 2008, 321, 1795-1799; J. Sharma, R. Chhabra, C. S. Andersen, K. V. Gothelf, H. Yan, Y. Liu, J. Am. Chem. Soc. 2008, 130, 7820-7821; R. J. Macfarlane, M. R. Jones, A. J. Senesi, K. L. Young, B. Lee, J. Wu, C. A. Mirkin, Angew. Chem. Int. Ed. 2010, 49, 4589-4592; A. M. Hung, C. M. Micheel, L. D. Bozano, L. W. Osterbur, G. M. Wallraff, J. N. Cha, Nat. Nanotechnol. 2010, 5, 121-126; B. Ding, Z. Deng, H. Yan, S. Cabrini, R. N. Zuckermann, J. Bokor, J. Am. Chem. Soc. 2010, 132, 3248-3249; Z. Zhao, E. L. Jacovetty, Y. Liu, H. Yan, Angew. Chem. Int. Ed. 2011, 50, 2041-2044.

[11] a) J.-H. Kim, J.-W. Kim, Langmuir 2010, 26, 18634-18638; b) J.-H. Kim, J.-W. Kim, Langmuir 2008, 24, 5667-5671.

[12] W. Yu, J. S. Lee, C. Johnson, J.-W. Kim, R. Deaton, IEEE Trans. Nanobioscience 2010, 9, 38-43; J.-W. Kim, D. P. Carpenter, R. Deaton, Nanomedicine 2005, 1, 220-230; R. Deaton, J.-W. Kim, J. Chen, Appl. Phys. Lett. 2003, 82, 1305-1307.

Thus, the invention provides, among other things, a nanoparticle assembly and a method of producing a nanoparticle assembly. Various features and advantages of the invention are set forth in the following claims.

What is claimed is:

1. A method of producing a DNA-nanoparticle complex utilizing an aqueous-phase anisotropic sequential ligand replacement technique, the method comprising:
   attaching a first DNA linker having a length of about 5 to about 100 nucleotides to a bead to form a first DNA-bead complex; and
   combining a nanoparticle comprising gold and having a diameter of about 1 nanometer to about 30 nanometers with the first DNA-bead complex to form a first nanoparticle-DNA-bead complex having one DNA linker attached to the nanoparticle and coupled to the bead;
   releasing the bead from the first nanoparticle-DNA-bead complex to form a first nanoparticle-DNA complex having one DNA linker attached to the nanoparticle;
   attaching a second DNA linker having a length of about 5 to about 100 nucleotides to a bead to form a second DNA-bead complex;
   combining the first nanoparticle-DNA complex with the second DNA-bead complex to form a second nanoparticle-DNA-bead complex having two DNA linkers attached to the nanoparticle; and
   releasing the bead from the second nanoparticle-DNA-bead complex to form a second nanoparticle-DNA complex having two DNA linkers attached to the nanoparticle that are approximately 180 degrees apart from one another.

2. The method of claim 1, wherein the two DNA linkers in the second nanoparticle-DNA complex are approximately parallel to one another.

3. The method of claim 2, further comprising:
   attaching a third DNA linker having a length of about 5 to about 100 nucleotides to a bead to form a third DNA-bead complex; and
   combining the second nanoparticle-DNA complex with the third DNA-bead complex to form a third nanoparticle-DNA-bead complex having three DNA linkers attached to the nanoparticle.

4. The method of claim 3, further comprising releasing the bead from the third nanoparticle-DNA-bead complex to form a third nanoparticle-DNA complex having three DNA linkers attached to the nanoparticle, wherein two of the three DNA linkers in the third nanoparticle-DNA complex are approximately parallel to one another and the third DNA linker is approximately perpendicular to the other DNA linkers.

5. The method of claim 4, further comprising:
   attaching a fourth DNA linker having a length of about 5 to about 100 nucleotides to a bead to form a fourth DNA-bead complex; and
   combining the third nanoparticle-DNA complex with the fourth DNA-bead complex to form a fourth nanoparticle-DNA-bead complex having four DNA linkers attached to the nanoparticle.

6. The method of claim 5, further comprising releasing the bead from the fourth nanoparticle-DNA-bead complex to form a fourth nanoparticle-DNA complex having four DNA linkers attached to the nanoparticle, wherein the four DNA linkers in the fourth nanoparticle-DNA complex form a square planar configuration in which each DNA linker is approximately parallel to one other DNA linker and approximately perpendicular to two other DNA linkers and all four DNA linkers are approximately coplanar.

7. The method of claim 6, further comprising:
   attaching a fifth DNA linker having a length of about 5 to about 100 nucleotides to a bead to form a fifth DNA-bead complex; and
   combining the fourth nanoparticle-DNA complex with the fifth DNA-bead complex to form a fifth nanoparticle-DNA-bead complex having five DNA linkers attached to the nanoparticle.

8. The method of claim 7, further comprising releasing the bead from the fifth nanoparticle-DNA-bead complex to form a fifth nanoparticle-DNA complex having five DNA linkers attached to the nanoparticle, wherein four of the five DNA linkers in the fifth nanoparticle-DNA complex form a square planar configuration in which each of the four DNA linkers is approximately parallel to one other DNA linker and approximately perpendicular to two other DNA linkers and all of the four DNA linkers are approximately coplanar, and wherein the fifth DNA linker is approximately perpendicular to each of the other four DNA linkers.

9. The method of claim 8, further comprising:
   attaching a sixth DNA linker having a length of about 5 to about 100 nucleotides to a bead to form a sixth DNA-bead complex; and
   combining the fifth nanoparticle-DNA complex with the sixth DNA-bead complex to form a sixth nanoparticle-DNA-bead complex having six DNA linkers attached to the nanoparticle.

10. The method of claim 9, further comprising releasing the bead from the sixth nanoparticle-DNA-bead complex to form a sixth nanoparticle-DNA complex having six DNA linkers attached to the nanoparticle, wherein the DNA linkers form an octahedral arrangement in which each DNA linker is approximately parallel to one other DNA linker and approximately perpendicular to the other four DNA linkers.

11. The method of claim 10, wherein at least two of the DNA linkers attached to the nanoparticle are different from each other.

12. The method of claim 1, further comprising purifying the first nanoparticle-DNA complex.

13. The method of claim 1, further comprising combining a complementary DNA nanoparticle complex with the first nanoparticle-DNA complex, wherein the complementary DNA-nanoparticle complex comprises a complementary DNA which hybridizes with the DNA of the first nanoparticle-DNA complex.

14. The method of claim 1, wherein the bead is negatively charged.

15. The method of claim 1, wherein the steps are carried out in an aqueous environment.

16. The method of claim 1, wherein the first DNA linker is shorter than a persistence length of double-stranded DNA.

17. The method of claim 1, wherein the first DNA linker includes a first end and a second end, wherein the first end includes a first functional group, and further comprising covalently or non-covalently binding the first functional group to the bead.

18. The method of claim 17, wherein the second end of the first DNA linker includes a second functional group, and further comprising covalently binding the second functional group to the nanoparticle.

19. The method of claim 18, wherein releasing the bead from the first nanoparticle-DNA-bead complex to form a first nanoparticle-DNA complex comprises breaking the bond between the first functional group and the bead.

20. The method of claim 19, wherein the steps are carried out in an aqueous environment, and wherein releasing the bead from the first nanoparticle-DNA-bead complex to form a first nanoparticle-DNA complex does not affect the bond between the second functional group and the nanoparticle.

* * * * *